United States Patent [19]

Imamura et al.

[11] Patent Number: 4,910,211
[45] Date of Patent: Mar. 20, 1990

[54] NOVEL BENZOTHIAZOLE AND ANTIRHEUMATIC AGENT COMPRISING IT AS AN ACTIVE INGREDIENT

[75] Inventors: Atsushi Imamura; Noriyuki Hori; Tadayuki Saito; Noriyasu Nishimura, all of Osaka; Masami Ohashi, Ibaraki; Kohichiro Yoshino, Suita, all of Japan

[73] Assignee: Kanebo Ltd., Tokyo, Japan

[21] Appl. No.: 229,919

[22] Filed: Aug. 8, 1988

[30] Foreign Application Priority Data

Aug. 7, 1987 [JP] Japan .................. 62-198669

[51] Int. Cl.$^4$ .................. C07D 277/66; A61K 31/425
[52] U.S. Cl. ..................... 514/367; 548/178
[58] Field of Search .................. 548/178; 514/367

[56] References Cited

FOREIGN PATENT DOCUMENTS 121704 7/1984 Japan .................. 548/178

OTHER PUBLICATIONS

Chemical Abstracts, vol. 104, No. 1, 21,26th, May 1986, p. 693.
J. Med. Chem., 29(5), 820–5, 1986.
Chemical Abstracts, vol. 104, pp. 1368 CS, 1986.
Chemical Abstracts, vol. 102, No. 5,12, 25th Mar. 1985, p. 27.

Primary Examiner—Robert Gerstl
Attorney, Agent, or Firm—Wenderoth, Lind & Ponack

[57] ABSTRACT

A benzothiazole of the following formula

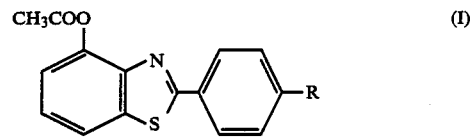

in which R represents a methyl, methoxy, carboxyl or methoxycarbonyl group. The compound is useful for treating rheumatic arthritis.

3 Claims, No Drawings

NOVEL BENZOTHIAZOLE AND ANTIRHEUMATIC AGENT COMPRISING IT AS AN ACTIVE INGREDIENT

This invention relates to a novel benzothiazole and an antirheumatic agent comprising it as an active ingredient.

More specifically, it relates to a benzothiazole represented by the following formula

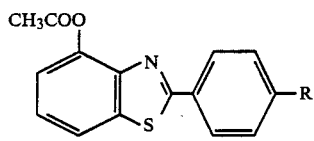

in which R represents a methyl, methoxy, carboxyl or methoxycarbonyl group, and an antirheumatic agent comprising it as an active ingredient.

Rheumatoid arthritis (RA for short) is a systemic inflammatory disease characterized by destructive, deformative and non-suppurative articular changes that become chronic with time. It is thought that RA is closely related to hereditary or environmental factors and caused by chronic inflammation due to an immune disorder triggered by viral infection. Treatment of RA has previously been performed mainly by symptomatic therapy with non-steroidal anti-inflammatory agents. Recently a therapy close to casual therapy by which the immune disorder is suppressed by an immunomodulatory effect has attracted attention. An example of a drug belonging to this type is lobenzarit disodium [N-(2-carboxyphenyl)-4-chloroanthranilic acid disodium salt, see Progress in Drug Research, 24, 185–186, edited by Ernst Jucker, published by Birkhäuser Verlag (1980)].

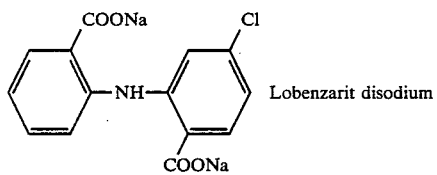

Lobenzarit disodium

J. Med. Chem., 1986, 29, 820–825 describes 5-acetoxy-2-(4-methylphenyl)benzothiazole (compound A), 6-acetoxy-2-(4-methylphenyl)benzothiazole (compound B) and 7-acetoxy-2-(4-methylphenyl)benzothiazole (compound C) but does not describe their pharmacological activity.

It is an object of this invention to provide a novel antirheumatic agent.

Another object of this invention is to provide a novel antirheumatic agent of the type which serves as an RA treating agent with immunomodulatory effect.

Still another object of this invention is to provide a novel benzothiazole used as an active ingredient in the antirheumatic agent of this invention, and an intermediate thereof.

Further objects of the invention along with its advantages will become apparent from the following description.

According to this invention, the objects and advantages of the invention are achieved firstly by a benzothiazole represented by the folllowing formula

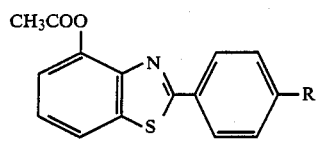

in which R represents a methyl, methoxy, carboxyl or methoxycarbonyl group.

The benzothiazole of formula (I) includes 4-acetoxy-2-(4-methylphenyl)benzothiazole, 4-acetoxy-2-(4-methoxyphenyl)benzothiazole, 4-(4-acetoxybenzothiazol-2-yl)benzoic acid, and methyl 4-(4-acetoxybenzothiazol-2-yl)benzoate.

The benzothiazole of formula (I) of this invention can be produced by reacting a compound of the following formula

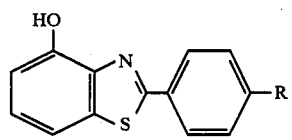

in which R is as defined, with an acetylating agent such as acetic anhydride or acetyl chloride in a customary manner.

Specifically, the compound (I) can be produced by reacting the compound (II) with the acetylating agent in an amount of 1.0 equivalent or more per equivalent of the compound (II) in the absence of solvent or in an inert organic solvent such as pyridine or dichloromethane, as required in the presence of a base such as pyridine or 4-dimethylaminopyridine, at a temperature from room temperature to a temperature under refluxing conditions for 1 to 3 hours.

The compound (II) used as the starting material in the above method is a novel compound which can be produced, for example by the following scheme.

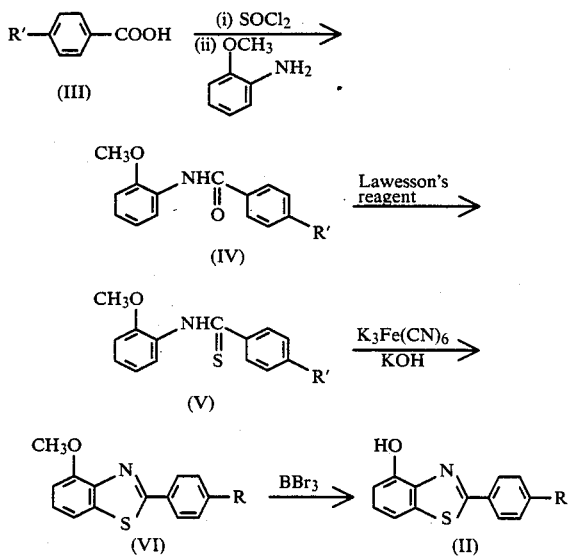

In the above scheme, R' represents a methyl, methoxy or methoxycarbonyl, and R is as defined.

Specifically, the compound (III) is reacted with thionyl chloride in the presence of a catalytic amount of N,N-dimethylformamide (DMF) to form the acid chloride, and it is then reacted with o-anisidine to obtain the compound (IV). Subsequently, the action of a Lawesson's reagent [2,4-bis(4-methoxyphenyl)-1,3-dithia-2,4-diphosphetane-2,4-disulfide] on the compound (IV) yields the compound (V) which is then reacted with potassium ferricyanide in the presence of potassium hydroxide to give the compound (VI). Action of boron tribromide on the compound (VI) gives the compound (II).

When R in formula (II) is a methyl group, it is preferred to use aluminum iodide in the presence of a catalytic amount of tetra-n-butylammonium iodide in the above final step instead of using boron tribromide. When R in formula (II) is a carboxyl group, it is preferred to use hydrobromic acid (47%) in the above final step (see Examples given hereinbelow).

The benzothiazole of this invention strongly suppresses the development of rat adjuvant arthritis, which is an animal model of RA, on the basis of their immunomodulatory effect, and yet has low toxicity. Accordingly, the benzothiazole of this invention is useful as an antirheumatic agent.

For use in the treatment of RA, the benzothiazole of this invention is usually applied as an orally administrable agent.

Oral dosage forms include, for example, solid formulations such as tablets, granules, powders and capsules, and liquid formulations such as syrups. The solid formulations are prepared by using ordinary drug additives such as lactose, corn starch, crystalline cellulose, carboxymethyl cellulose calcium, hydroxypropyl cellulose and magnesium stearate. The capsules may be obtained by filling the granules or powders so prepared in suitable capsules. The syrups may be obtained by dissolving or suspending the compound of this invention in an aqueous solution containing sugar, ethyl p-hydroxybenzoate or propyl p-hydroxybenzoate, for example.

The dosage of the compound of this invention can be varied according to the condition, age, etc. of the patient, but is usually 0.1 to 15.0 mg/kg per day for adults. This dosage is administered once or in two or three divided portions a day.

The pharmacological activity of the compounds of this invention will be described.

The compound of this invention showed clearly stronger suppressive effect on the development of rat adjuvant arthritis, an animal model of RA, than lobenzarit disodium and the compounds A, B and C mentioned above (see Test Example 1).

From the following facts (i) and (ii), the suppressive effect of the compound of this invention on the development of adjuvant arthritis is considered to be based not on anti-inflammatory effect but on immunomodulatory effect.

(i) The compound of this invention, like lobenzarit disodium, shows no effect on rat carrageenin-induced paw edema, a model of acute inflammation, and on rat mustard-induced paw edema, a model of subacute inflammation (in either case, no effect in a dose of 100 mg/kg).

(ii) Effect on cellular immunity was studied using delayed-type hypersensitivity as an index. The compound of this invention, like lobenzarit disodium, suppresses an abnormally enhanced immune reaction, but shows no effect on a normal immune reaction (see Test Example 2).

The compound of this invention showed lower toxicity than lobenzarit disodium (see Test Example 3).

Hence, the benzothiazole of this invention strongly suppresses the development of adjuvant arthritis on the basis of their immunomodulatory effect and has low toxicity. Hence the benzothiazole of this invention is useful as an antirheumatic agent.

TEST EXAMPLE 1

Effect on the Development of Adjuvant Arthritis Test Compounds (1) The compounds of Examples 5 to 8 (invention)
(2) Compounds A, B and C (comparison; described in the above-cited reference)
(3) Lobenzarit disodium (comparison)

Method

Fischer male rats (8 weeks old; body weight 120–180 g) were grouped so that the average of body weights among the groups were nearly the same. Then, 0.1 ml of complete adjuvant obtained by suspending *Mycobacterium butyricum* (Difco Laboratories) in paraffin oil in a concentration of 6 mg/ml was injected into the footpad of the right hind paw to induce adjuvant arthritis.

Each of the test compounds was dissolved or suspended in a 1% gum arabic solution, and administered orally once a day on six days a week over a period of three weeks starting from the day of the adjuvant injection. The group administered with a 1% gum arabic solution instead of the test compound was served for a control. The volumes of both hind paws were measured plethysmographically by displacement of water at various times after injection of the adjuvant, and the percent paw edema inhibition was calculated from the following equation.

$$\text{Paw edema inhibition (\%)} = \left(1 - \frac{E_{exp}}{E_{cont}}\right) \times 100$$

$E_{exp}$: the percent paw edema in rats treated with the test compound
$E_{cont}$: the mean of percent paw edema in rats of the control group The percent paw edema was calculated from the following equation.

$$\text{Paw edema (\%)} = \frac{V_{post} - V_{pre}}{V_{pre}} \times 100$$

$V_{post}$: the paw volume after treatment with the adjuvant
$V_{pre}$: the paw volume before treatment with the adjuvant Results Table 1 shows percent paw edema inhibitions by the compounds calculated 21 days after injection of the adjuvant.

TABLE 1

| Test compound | | Dose (mg/kg) | N | Paw edema inhibition (%, mean ± standard error) | |
|---|---|---|---|---|---|
| | | | | Treated paw | Non-treated paw |
| Example | 5 | 100 | 24 | 31.8 ± 3.9 | 32.0 ± 7.7 |
| | 6 | 100 | 24 | 24.7 ± 3.7 | 27.4 ± 10.8 |
| | 7 | 100 | 24 | 29.9 ± 2.9 | 38.5 ± 6.0 |
| | 8 | 100 | 24 | 29.3 ± 3.6 | 28.6 ± 8.8 |
| Com- | A | 100 | 16 | 12.9 ± 4.4 | 4.5 ± 11.7 |

TABLE 1-continued

| Test compound | | Dose (mg/kg) | N | Paw edema inhibition (%, mean ± standard error) | |
|---|---|---|---|---|---|
| | | | | Treated paw | Non-treated paw |
| pound | B | 100 | 8 | −7.6 ± 8.8 | 4.4 ± 14.2 |
| | C | 100 | 24 | 16.6 ± 4.1 | 8.9 ± 10.4 |
| Lobenzarit disodium | | 50 | 16 | 6.3 ± 5.3 | −9.0 ± 12.0 |
| | | 100 | 12* | 15.1 ± 6.6 | −1.7 ± 11.4 |

*Four animals out of 16 could not be included in the data because of death during the test.

Table 1 showed that the compound of this invention had a clear inhibitory effect on edema of the rat hind paws treated or non-treated with the adjuvant, and this effect was evidently stronger than those of lobenzarit disodium and the compounds A, B and C.

TEST EXAMPLE 2

Effect on Delayed-Type Hypersensitivity (DTH)

(A) Effect on a normal immune reaction

Test Compounds (1) the compound of Example 5 (invention)
(2) Lobenzarit disodium (comparison)

Method

BALB/c male mice (8 weeks old) were sensitized by injection into the tail vein with 0.2 ml of $5 \times 10^6$/ml sheep red blood cells (SRBC). Three days after the sensitization, 0.05 ml of $8 \times 10^9$/ml SRBC was injected into the footpad of the right hind paw for elicitation of DTH. Footpad thickness was measured immediately before and 24 hours after the elicitation with a dial thickness gauge. The level of DTH was expressed as footpad swelling (mm) at 24 hour. The inhibition (%) of footpad swelling was calculated from the following equation.

The test compound was dissolved or suspended in a 1% gum arabic solution, and administered orally once a day over a period of 7 days starting from four days before the sensitization. To a control group, a 1% gum arabic solution was administered instead of the test compound.

$$\text{Footpad swelling inhibition (\%)} = \left(1 - \frac{T_{exp}}{T_{cont}}\right) \times 100$$

$T_{exp}$: the mean of the footpad swelling in mice treated with the test compound
$T_{cont}$: the mean of the footpad swelling in mice of the control group Results The results are shown in Table 2.

TABLE 2

| Dose (mg/kg) | N | Footpad swelling (× $10^{-2}$ mm, mean ± standard error) [Footpad swelling inhibition, %] | |
|---|---|---|---|
| | | Compound of Example 5 | Lobenzarit disodium |
| 1 | 7 | 59 ± 5 [0.0] | 67 ± 2 [4.3] |
| 3 | 7 | 63 ± 6 [−6.8] | 64 ± 5 [8.6] |
| 10 | 7 | 57 ± 6 [3.4] | 76 ± 6 [−8.6] |
| 30 | 7 | 64 ± 6 [−8.5] | 65 ± 4 [7.1] |
| 100 | 7 | 53 ± 4 [10.2] | 65 ± 5 [7.1] |

TABLE 2-continued

| Dose (mg/kg) | N | Footpad swelling (× $10^{-2}$ mm, mean ± standard error) [Footpad swelling inhibition, %] | |
|---|---|---|---|
| | | Compound of Example 5 | Lobenzarit disodium |
| — | 7 | 59 ± 6 [—] | 70 ± 2 [—] |

Table 2 showed that the compound of this invention, like lobenzarit disodium, did not inhibit footpad swelling at any doses, and consequently did not affect DTH in a normal immune reaction.

(B) Effect on an enhanced immune reaction

Test compounds

Same as in (A) above.

Method

Cyclophosphamide (75 mg/kg) was administered intraperitoneally to BALB/c male mice (8 weeks old), and four days later, the mice were sensitized by injection into the tail vein with 0.2 ml of $5 \times 10^7$/ml SRBC. Three days after the sensitization, 0.05 ml of $8 \times 10^9$/ml SRBC was injected into the footpad of the right hind paw for elicitation of DTH. Twenty four hours later, footpad swelling (mm) was measured in the same way as in (A) above, and the inhibition (%) of footpad swelling was calculated from the following equation.

The test compound was dissolved or suspended in a 1% gum arabic solution, and administered orally once a day over a period of 7 days starting from four days before the sensitization (immediately after administration of cyclophosphamide). To a control group, a 1% gum arabic solution was administered instead of the test compound. The group, administered with physiological saline instead of cyclophosphamide and a 1% gum arabic solution instead of test compound respectively, was served for a normal group.

$$\text{Footpad swelling inhibition (\%)} = \left(\frac{T_{cont} - T_{exp}}{T_{cont} - T_{nor}}\right) \times 100$$

$T_{cont}$: the mean of the footpad swelling in mice of the control group
$T_{exp}$: the mean of the footpad swelling in mice treated with the test compound
$T_{nor}$: the mean of the footpad swelling in mice of the normal group.

Results

The results are shown in Table 3.

TABLE 3

| Dose (mg/kg) | | N | Footpad swelling (× $10^{-2}$ mm, mean ± standard error) [Footpad swelling inhibition, %] | |
|---|---|---|---|---|
| Cyclo-phosphamide | Test compound | | Compound of Example 5 | Lobenzarit disodium |
| 75 | 1 | 7 | 37 ± 5* [57.1] | 47 ± 3 [20.0] |
| 75 | 3 | 7 | 35 ± 1** [66.7] | 43 ± 3 [40.0] |
| 75 | 10 | 7 | 31 ± 3** [85.7] | 53 ± 3 [−10.0] |
| 75 | 30 | 7 | 33 ± 2** [76.2] | 41 ± 3* [50.0] |
| 75 | 100 | 7 | 37 ± 4* [57.1] | 41 ± 3* [50.0] |
| — | — | 7 | 28 ± 2*** [—] | 31 ± 2*** [—] |

TABLE 3-continued

| Dose (mg/kg) | | | Footpad swelling ($\times 10^{-2}$ mm, mean ± standard error) [Footpad swelling inhibition, %] | |
|---|---|---|---|---|
| Cyclo-phosphamide | Test compound | N | Compound of Example 5 | Lobenzarit disodium |
| 75 | — | 7 | 49 ± 3 [—] | 51 ± 4 [—] |

*$P < 0.05$, significantly different from the control group (t-test).
**$P < 0.01$, significantly different from the control group (t-test).
***$P < 0.001$, significantly different from the control group (t-test).

Table 3 showed that the compound of this invention at any doses inhibited footpad swelling significantly, and consequently inhibited DTH in an enhanced immune reaction. This effect was evidently stronger than that of lobenzarit disodium.

TEST EXAMPLE 3

Acute Toxicity

Test Compounds (1) The Compounds of Examples 5 to 8 (invention)
(2) Lobenzarit diodium (comparison)

Method ddY male mice (body weight about 23 g) were fasted overnight, and the test compound dissolved or suspended in a 1% gum arabic solution administered orally. From the number of mice died within a week, the $LD_{50}$ value was calculated by the probit method.

Results

The results are shown in Table 4.

TABLE 4

| Test compound | | N | $LD_{50}$ (mg/kg) |
|---|---|---|---|
| Example | 5 | 5 | >3,000 |
| | 6 | 5 | >3,000 |
| | 7 | 5 | 2,020 |
| | 8 | 5 | >3,000 |
| Lobenzarit disodium | | 5 | 593 |

The dosage of the benzothiazole of this invention can alleviate, improve or resolve the symptoms of the patient with RA.

The following Examples further illustrate the present invention specifically.

EXAMPLE 1

4-Hydroxy-2-(4-methylphenyl)benzothiazole (1) 4-Methyl-2'-methoxybenzanilide

A catalytic amount of DMF (ca. 0.5 ml) was added to a mixture of 33.0 g of p-methylbenzoic acid and 80 ml of thionyl chloride, and the mixture was refluxed for 3 hours. After the reaction, the reaction mixture was dried under reduced pressure. The residue was dissolved in 40 ml of tetrahydrofuran, and added dropwise to a solution of 29.8 g of o-anisidine in 190 ml of pyridine at 5° to 10° C. After stirring the mixture at room temperature for 1 hour, it was poured into 2.5 liters of water. The precipitated crystals were collected by filtration, washed with water and dried. Recrystallization from cyclohexane gave 50.5 g of 4-methyl-2'-methoxybenzanilide. mp 72.5°–74.5° C.

(2) 4-Methyl-2'-methoxybenzothioanilide

The 4-methyl-2'-methoxybenzanilide (50.0 g) obtained in (1) was dissolved in 200 ml of toluene, and 46.1 g of Lawesson's reagent was added. The mixture was refluxed for 1 hour. After the reaction, the reaction mixture was cooled to about 50° C., and 200 ml of water was added. The mixture was further refluxed for 2 hours. The organic layer was separated, washed with water and dried over anhydrous magnesium sulfate. The solvent was evapoated under reduced pressure. The residue was recrystallized from methanol and then cyclohexane to give 31.9 g of 4-methyl-2'-methoxybenzothioanilide. mp 91.0°–93.0° C.

(3) 2-(4-Methylphenyl)-4-methoxybenzothiazole

Potassium hydroxide (21.8 g) and 64.0 g of potassium ferricyanide were dissolved in 2.5 liters of water, and with stirring, 25.0 g of 4-methyl-2'-methoxybenzothioanilide obtained in (2) was added, and the mixture was stirred at room temperature for 6 hours. After the reaction, the crystals were collected by filtration, washed with water and dried. Recrystallization from cyclohexane gave 13.9 g of 2-(4-methylphenyl)-4-methoxybenzothiazole. mp 98.0°–100.0° C.

(4) 4-Hydroxy-2-(4-methylphenyl)benzothiazole

Aluminum powder (1.4 g) and 10.9 g of iodine were added to 50 ml of benzene. The mixture was refluxed in a stream of nitrogen until the color of iodine disappeared. A solution of 11.4 g of 2-(4-methylphenyl)-4-methoxybenzothiazole obtained in (3) and 31 mg of tetra-n-butylammonium iodide in 100 ml of benzene was added dropwise. The mixture was refluxed for 7 hours, and then poured into 200 ml of water, extracted with ethyl acetate three times, and dried over anhydrous magnesium sulfate. The solvent was evaporated under reduced pressure. The residue was washed with a small amount of chloroform, and recrystallized from acetonitrile to give 7.8 g of 4-hydroxy-2-(4-methylphenyl)benzothiazole. mp 163.5°–165.5° C.

EXAMPLE 2

4-Hydroxy-2-(4-methoxyphenyl)benzothiazole (1) 4-Methoxy-2'-methoxybenzothioanilide 4-Methoxy-2'-methoxybenzanilide (29.5 g) [Bull. Soc. Chim. France, 1964, (5), 924–935] was dissolved in 150 ml of toluene, and 25.6 g of Lawesson's reagent was added. The mixture was refluxed for 4.5 hours. After the reaction, the solvent was evaporated under reduced pressure. The residue was subjected to silica gel column chromatography [eluted with cyclohexane/ethyl acetate (7/1, v/v)] to give 26.5 g of 4-methoxy-2'-methoxybenzothioanilide.

A portion of this product was recrystallized from cyclohexane to give a product having a melting point of 84.5° to 86.5° C.

(2) 4-Methoxy-2-(4-methoxyphenyl)benzothiazole

Potassium hydroxide (20.8 g) and 61.2 g of potassium ferricyanide were dissolved in 2.4 liters of water, and with stirring, 25.4 g of 4-methoxy-2'-methoxybenzothioanilide obtained in (1) was added. The mixture was stirred at room temperature for 10 hours. After the reaction, the crystals were collected by filtration, washed with water and dried. The crystals were subjected to silica gel column chromatography [eluted with cyclohexane/ethyl acetate (7/1, v/v)]. Recrystallization from cyclohexane gave 12.0 g of 4-methoxy-2-(4-methoxyphenyl)benzothiazole. mp 86.0°–88.0° C.

(3) 4-Hydroxy-2-(4-methoxyphenyl)benzothiazole

The 4-methoxy-2-(4-methoxyphenyl)benzothiazole (9.0 g) obtained in (2) was dissolved in 15 ml of dichloromethane, and a solution of 8.7 g of boron tribromide in 15 ml of dichloromethane was added dropwise to the solution. The mixture was stirred at room temperature for 2 hours, and then poured into 200 ml of ice water, followed by extraction with chloroform three times. The extract was dried over anhydrous magnesium sulfate, and the solvent was evaporated under reduced pressure. The residue was subjected to silica gel column chromatography (eluted with chloroform) to give 4.2 g of 4-hydroxy-2-(4-methoxyphenyl)benzothiazole.

A portion of this product was recrystallized from cyclohexane and ethyl acetate to give a product having a melting point of 128.0° to 130.0° C.

EXAMPLE 3

4-(4-Hydroxybenzothiazol-2-yl)benzoic acid (1) 4-Methoxycarbonyl-2'-methoxybenzanilide A catalytic amount of DMF (ca. 0.5 ml) was added to a mixture of 102.4 g of p-methoxycarbonylbenzoic acid and 160 ml of thionyl chloride, and the mixture was refluxed for 1.5 hours. After the reaction, the reaction mixture was dried under reduced pressure. The residue was dissolved in 90 ml of tetrahydrofuran, and the solution was added dropwise at 5°–10° C. to a solution of 70.0 g of o-anisidine in 440 ml of pyridine. The mixture was stirred at room temperature for 2 hours, and then poured into 4 liters of water. The crystals that precipitated were collected by filtration, washed with water and dried to give 160.8 g of 4-methoxycarbonyl-2'-methoxybenzanilide.

A portion of the product was recrystallized from cyclohexane and ethyl acetate to give a product having a melting point of 119.0° to 121.0° C.

(2) 4-Methoxycarbonyl-2'-methoxybenzothioanilide

The 4-methoxycarbonyl-2'-methoxybenzanilide (123.2 g) obtained in (1) was dissolved in 400 ml of toluene, and 96.1 g of Lawesson's reagent was added. The mixture was refluxed for 2 hours. After the reaction, the reaction mixture was hot-filtered. The filtrate was left to stand until it cooled to room temperature. The precipitated crystals were collected by filtration and washed with a small amount of benzene to give 69.2 g of 4-methoxycarbonyl-2'-methoxybenzothioanilide.

A portion of this product was recrystallized from cyclohexane and ethyl acetate to give a product having a melting point of 105.0° to 107.0° C.

(3) 4-(4-Methoxybenzothiazol-2-yl)benzoic acid and methyl 4-(4-methoxybenzothiazol-2-yl)benzoate Potassium hydroxide (52.2 g) and 230.0 g of potassium ferricyanide were dissolved in 3 liters of water, and with stirring, 70.0 g of 4-methoxycarbonyl-2'-methoxybenzothioanilide obtained in (2) was added. The mixture was stirred at room temperature for 3.5 hours. After the reaction, the crystals were collected by filtration, washed with water, dried and subjected to silica gel column chromatography [eluted with benzene/ethyl acetate (97/3, v/v)]. Recrystallization from cyclohexane gave 13.1 g of methyl 4-(4-methoxybenzothiazol-2-yl)benzoate. mp 165.0°–167.0° C.

The filtrate from which the crystals were collected by filtration after the reaction was acidified with concentrated hydrochloric acid. The precipitated crystals were collected by filtration, washed with water and dried to give 31.0 g of 4-(4-methoxybenzothiazol-2-yl)benzoic acid.

A portion of the product was recrystallized from dioxane to give a product having a melting point of 289.0° to 291.0° C.

(4) The 4-(4-hydroxybenzothiazol-2-yl)benzoic acid 4-(4-Methoxybenzothiazol-2-yl)benzoic acid (7.8 g) obtained in (3) was added to 180 ml of hydrobromic acid (47%), and the mixture was refluxed for 27 hours. After the reaction, the mixture was poured into 180 ml of water. The crystals were collected by filtration, washed with water, dried, and then further washed with chloroform. Recrystallization from dioxane gave 7.0 g of 4-(4-hydroxybenzothiazol-2-yl)benzoic acid.

A portion of the product was subjected to silica gel column chromatography [eluted with chloroform/methanol (98/2, v/v)], and recrystallized from isopropanol and then from dioxane to give a product having a melting point of 290.0° to 302.0° C. (decomp.).

EXAMPLE 4

Methyl 4-(4-hydroxybenzothiazol-2-yl)benzoate

The methyl 4-(4-methoxybenzothiazol-2-yl)benzoate (11.3 g) obtained in Example 3 (3) was dissolved in 200 ml of dichloromethane, and a solution of 9.5 g of boron tribromide in 80 ml of dichloromethane was added dropwise to the solution. The mixture was stirred at room temperature for 2.5 hours, then poured into 300 ml of ice water, extracted with chloroform three times, and dried over anhydrous magnesium sulfate. The solvent was evaporated under reduced pressure. The residue was subjected to silica gel column chromatography (eluted with chloroform), and the solvent was evaporated under reduced pressure. The residue was washed with a small amount of chloroform, and recrystallized from ethyl acetate to give 3.6 g of methyl 4-(4-hydroxybenzothiazol-2-yl)benzoate. mp 215°–219.0° C.

EXAMPLE 5

4-Acetoxy-2-(4-methylphenyl)benzothiazole

The 4-hydroxy-2-(4-methylphenyl)benzothiazole (5.8 g) obtained in Example 1 was added to 58 ml of acetic anhydride and refluxed for 3 hours. After the reaction, the reaction mixture was dried under reduced pressure. The residue was washed with a small amount of cyclohexane, and recrystallized from cyclohexane to give 4.8 g of 4-acetoxy-2-(4-methylphenyl)benzothiazole. mp 110.0°–113.0° C.

NMR (CDCl$_3$, δ ppm): 2.42(3H, s), 2.48(3H, s), 7.20(1H, dd), 7.28(2H, d), 7.36(1H, dd), 7.76(1H, dd), 7.96(2H, d).

Elemental analysis value (for $C_{16}H_{13}NO_2S$) Calculated (%) C, 67.82; H, 4.62; N, 4.94. Found (%) C, 68.11; H, 4.58; N, 5.07.

EXAMPLE 6

4-Acetoxy-2-(4-methoxyphenyl)benzothiazole

The 4-hydroxy-2-(4-methoxyphenyl)benzothiazole (4.0 g) obtained in Example 2 was added to 40 ml of acetic anhydride, and the mixture was refluxed for 1 hour. After the reaction, the reaction mixture was dried under reduced pressure. The residue was washed with a small amount of cyclohexane, and recrystallized from cyclohexane and ethyl acetate to give 4.0 g of 4-acetoxy-2-(4-methoxyphenyl)benzothiazole.

mp 121.5°–124.5° C.

NMR (CDCl$_3$, δ ppm): 2.48(3H, s), 3.82(3H, s), 6.94(2H, d), 7.16(1H, dd), 7.30(1H, dd), 7.70(1H, dd), 7.98(2H, d).

Elemental analysis value (for $C_{16}H_{13}NO_3S$) Calculated (%) C, 64.20; H, 4.38; N, 4.68. Found (%) C, 64.29; H, 4.43; N, 4.59.

EXAMPLE 7

4-(4-Acetoxybenzothiazol-2-yl)benzoic acid

The 4-(4-hydroxybenzothiazol-2-yl)benzoic acid (6.9 g) obtained in Example 3 was dissolved in 15 ml of pyridine, and 2.6 g of acetic anhydride was added dropwise. The mixture was stirred at room temperature for 2 hours, and 160 ml of cyclohexane was added. The precipitated crystals were collected by filtration, washed with cyclohexane and then diethyl ether, and recrystallized from acetonitrile to give 4.0 g of 4-(4-acetoxybenzothiazol-2-yl)benzoic acid.

mp 229.0°–233.0° C.

NMR (DMSO-$d_6$, δ ppm): 2.48(3H, s), 7.38(1H, dd), 7.54(1H, dd), 8.0–8.3(5H, m), 12.8–13.6(1H, bs).

Elemental analysis value (for $C_{16}H_{11}NO_4S$) Calculated (%) C, 61.33; H, 3.54; N, 4.47. Found (%) C, 61.38; H, 3.41; N, 4.32.

EXAMPLE 8

Methyl 4-(4-acetoxybenzothiazol-2-yl)benzoate

The methyl 4-(4-hydroxybenzothiazol-2-yl)benzoate (2.5 g) obtained in Example 4 was added to 30 ml of acetic anhydride, and the mixture was refluxed for 2 hours. After the reaction, the reaction mixture was dried under reduced pressure. The residue was washed with a small amount of cyclohexane, and recrystallized from cyclohexane and ethyl acetate to give 2.3 g of methyl 4-(4-acetoxybenzothiazol-2-yl)benzoate.

mp 143.5°–145.5° C.

NMR (CDCl$_3$, δ ppm): 2.50(3H, s), 3.94(3H, s), 7.20(1H, dd), 7.38(1H, dd), 7.74(1H, dd), 8.0–8.2(4H, m).

Elemental analysis value (for $C_{17}H_{13}NO_4S$) Calculated (%) C, 62.37; H, 4.00; N, 4.28. Found (%) C, 62.32; H, 3.98; N, 4.34.

EXAMPLE 9

Preparation of tablets:

| Ingredient | Recipe Amount (g) |
|---|---|
| 4-Acetoxy-2-(4-methyl-phenyl)benzothiazole (compound of Example 5) | 500 |
| Lactose | 700 |
| Crystalline cellulose | 400 |
| Carboxymethyl cellulose calcium | 150 |
| Hydroxypropyl cellulose | 30 |
| Magnesium stearate | 20 |
| Total | 1,800 |

Procedure

The compound of Example 5, lactose and crystalline cellulose were uniformly mixed. Hydroxypropyl cellulose was dissolved in 600 g of purified water, and the solution was added to the above mixture. They were kneaded, and the kneaded mixture was passed through a crusing-granulating machine (2 mm screen) and then dried for 20 minutes by a fluidized bed granulator (80° C.). Crystalline cellulose, carboxymethyl cellulose calcium and magnesium stearate were added and mixed. The mixture was tableted to give tablets (180 mg tablets, diameter 8 mm) each containing 50 mg of the compound of Example 5.

EXAMPLE 10

Preparation of a powder:

| Ingredient | Recipe Amount (g) |
|---|---|
| 4-Acetoxy-2-(4-methoxy-phenyl)benzothiazole (compound of Example 6) | 100 |
| Lactose | 600 |
| Corn starch | 290 |
| Magnesium stearate | 10 |
| Total | 1,000 |

Procedure

The above ingredients were fully mixed to form a uniform mixed powder to obtain a powder containing 100 mg of the compound of Example 6 as an active ingredient per gram.

EXAMPLE 11

Preparation of granules:

| Ingredient | Recipe Amount (g) |
|---|---|
| 4-(4-Acetoxybenzothiazol-2-yl)benzoic acid (compound of Example 7) | 100 |
| Lactose | 400 |
| Corn starch | 280 |
| Crystalline cellulose | 200 |
| Hydroxypropyl cellulose | 20 |
| Total | 1,000 |

Procedure

The compound of Example 7, lactose, corn starch and crystalline cellulose were uniformly mixed. A solution of hydroxypropyl cellulose in 400 g of purified water was added to the mixture, and they were kneaded. The kneaded mixture was passed through an extrusion granulator (0.8 mm screen), and dried in a fluidized bed granulator at 80° C. for 20 minutes. The granules wee sieved by a 14-mesh sieve to obtain granules containing 100 mg of the compound of Example 7 per gram.

EXAMPLE 12

Preparation of capsules agents:

| Ingredient | Recipe Amount (g) |
|---|---|
| Methyl 4-(4-Acetoxybenzothiazol-2-yl)benzoate (compound of Example. 8) | 500 |
| Lactose | 970 |
| Crystalline cellulose | 600 |
| Corn starch | 400 |
| Magnesium stearate | 30 |
| Total | 2,500 |

Procedure

The above ingredients were fully mixed, and filled in No. 3 hard capsules to prepare a capsular agent containing 50 mg of the compound of Example 8 as an active ingrediet per capsule (250 mg).

We claim:

1. A benzothiazole of the following formula

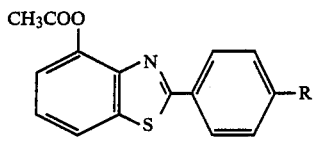

in which R represents a methyl, methoxy, carboxyl or methoxycarbonyl group.

2. An antirheumatic composition which comprises as an active ingredient in immunomodulatorily effective amount of a benzothiazole of the following formula

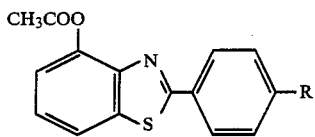

in which R represents a methyl, methoxy, carboxyl or methoxycarbonyl group, in admixture with a pharmaceutically acceptable carrier or diluent.

3. A method of treating rheumatic arthritis which comprises administering to rheumatic patients an immunomodulatorily effective amount of a benzothiazole of the following formula

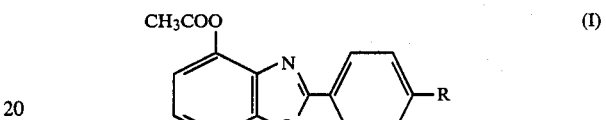

in which R represents a methyl, methoxy, carboxyl or methoxycarbonyl group.

* * * * *